(12) United States Patent
Kato et al.

(10) Patent No.: US 11,314,076 B2
(45) Date of Patent: Apr. 26, 2022

(54) RIGID SCOPE

(71) Applicant: OLYMPUS CORPORATION, Hachioji (JP)

(72) Inventors: Takayuki Kato, Tokyo (JP); Takahiro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 294 days.

(21) Appl. No.: 16/591,509

(22) Filed: Oct. 2, 2019

(65) Prior Publication Data

US 2020/0033583 A1 Jan. 30, 2020

Related U.S. Application Data

(63) Continuation of application No. PCT/JP2018/008906, filed on Mar. 8, 2018.

(30) Foreign Application Priority Data

Apr. 7, 2017 (JP) .............................. JP2017-076475

(51) Int. Cl.
*G02B 23/24* (2006.01)
*A61B 1/002* (2006.01)
(Continued)

(52) U.S. Cl.
CPC ............ *G02B 23/243* (2013.01); *A61B 1/002* (2013.01); *A61B 1/00096* (2013.01);
(Continued)

(58) Field of Classification Search
CPC ........ G02B 23/243; G02B 9/60; G02B 13/04; G02B 23/2476; G02B 7/021; G02B 23/2446; A61B 1/00096; A61B 1/002
See application file for complete search history.

(56) References Cited

U.S. PATENT DOCUMENTS 5,632,718 A 5/1997 Igarashi et al.
5,902,232 A 5/1999 Igarashi
(Continued)

FOREIGN PATENT DOCUMENTS

DE 102009009016 A1 * 8/2010 ............. A61B 1/307
EP 2165640 A1 3/2010
(Continued)

OTHER PUBLICATIONS

Machine translation of DE102009009016 retrieved electronically from Espacenet Sep. 17, 2021 (Year: 2021).*
(Continued)

*Primary Examiner* — Cara E Rakowski
(74) *Attorney, Agent, or Firm* — Holtz, Holtz & Volek PC

(57) ABSTRACT

A rigid scope includes: an objective lens composed of, in order from an object side to an image side, a first lens group having a negative power, a second lens group including a lens having a positive power, and a third lens group including two or more lenses; a relay lens arranged on the image side of the objective lens; a first lens frame that fixes in place a front group including at least the first lens group and the second lens group of the objective lens; and a second lens frame that fixes in place a rear group including one or more remaining lenses constituting the objective lens and at least part of the relay lens.

8 Claims, 11 Drawing Sheets

(51) Int. Cl.
- *G02B 7/02* (2021.01)
- *G02B 9/60* (2006.01)
- *G02B 13/04* (2006.01)
- *A61B 1/00* (2006.01)

(52) U.S. Cl.
CPC .............. *G02B 7/021* (2013.01); *G02B 9/60* (2013.01); *G02B 13/04* (2013.01); *G02B 23/2446* (2013.01); *G02B 23/2476* (2013.01)

(56) References Cited

U.S. PATENT DOCUMENTS

| | | | |
|---|---|---|---|
| 2004/0109243 A1 | 6/2004 | Orimo et al. | |
| 2005/0180025 A1 | 8/2005 | Orimo et al. | |
| 2010/0076268 A1 | 3/2010 | Takasugi et al. | |
| 2013/0176638 A1* | 7/2013 | Schouwink | A61B 1/00179 359/834 |
| 2016/0170228 A1 | 6/2016 | Yamagami | |
| 2016/0353977 A1* | 12/2016 | Kibayashi | G02B 23/243 |

FOREIGN PATENT DOCUMENTS

| | | |
|---|---|---|
| JP | H07248454 A | 9/1995 |
| JP | H11142729 A | 5/1999 |
| JP | 2002095626 A | 4/2002 |
| JP | 2004163865 A | 6/2004 |
| JP | 2007133175 A | 5/2007 |
| JP | 3989806 B2 | 10/2007 |
| JP | 2009053340 A | 3/2009 |
| JP | 2010097208 A | 4/2010 |
| JP | 2010134376 A * | 6/2010 |
| JP | 2010134376 A | 6/2010 |
| JP | 2012141536 A | 7/2012 |
| JP | 2013536458 A | 9/2013 |
| JP | 5558058 B2 | 7/2014 |
| WO | 2015025831 A1 | 2/2015 |

OTHER PUBLICATIONS

International Search Report (ISR) dated Jun. 12, 2018 issued in International Application No. PCT/JP2018/008906.
Written Opinion dated Jun. 12, 2018 issued in International Application No. PCT/JP2018/008906.

* cited by examiner

US 11,314,076 B2

RIGID SCOPE

CROSS-REFERENCE TO RELATED APPLICATIONS

This is a continuation of International Application PCT/JP2018/008906, with an international filing date of Mar. 8, 2018, which is hereby incorporated by reference herein in its entirety. This application claims the benefit of Japanese Patent Application No. 2017-076475, the content of which is incorporated herein by reference.

TECHNICAL FIELD

The present invention relates to a rigid scope.

BACKGROUND ART

Heretofore, in rigid scopes, image quality adjustment has been performed in order to reduce image plane tilt by moving a negative power lens located at the leading end of the objective lens of an optical system including the objective lens in a direction perpendicular to the optical axis (for example, refer to Patent Document 1).

CITATION LIST

Patent Literature

{PTL 1} Japanese Unexamined Patent Application Publication No. 11-142729

SUMMARY OF INVENTION

An aspect of the present invention is directed to a rigid scope that includes: an objective lens composed of, in order from an object side to an image side, a first lens group having a negative power, a second lens group including a lens having a positive power, and a third lens group including two or more lenses; a relay lens arranged on the image side of the objective lens; a first lens frame that fixes in place a front group including at least the first lens group and the second lens group of the objective lens; and a second lens frame that fixes in place a rear group including one or more remaining lenses constituting the objective lens and at least part of the relay lens.

DESCRIPTION OF EMBODIMENTS

Figure 1:
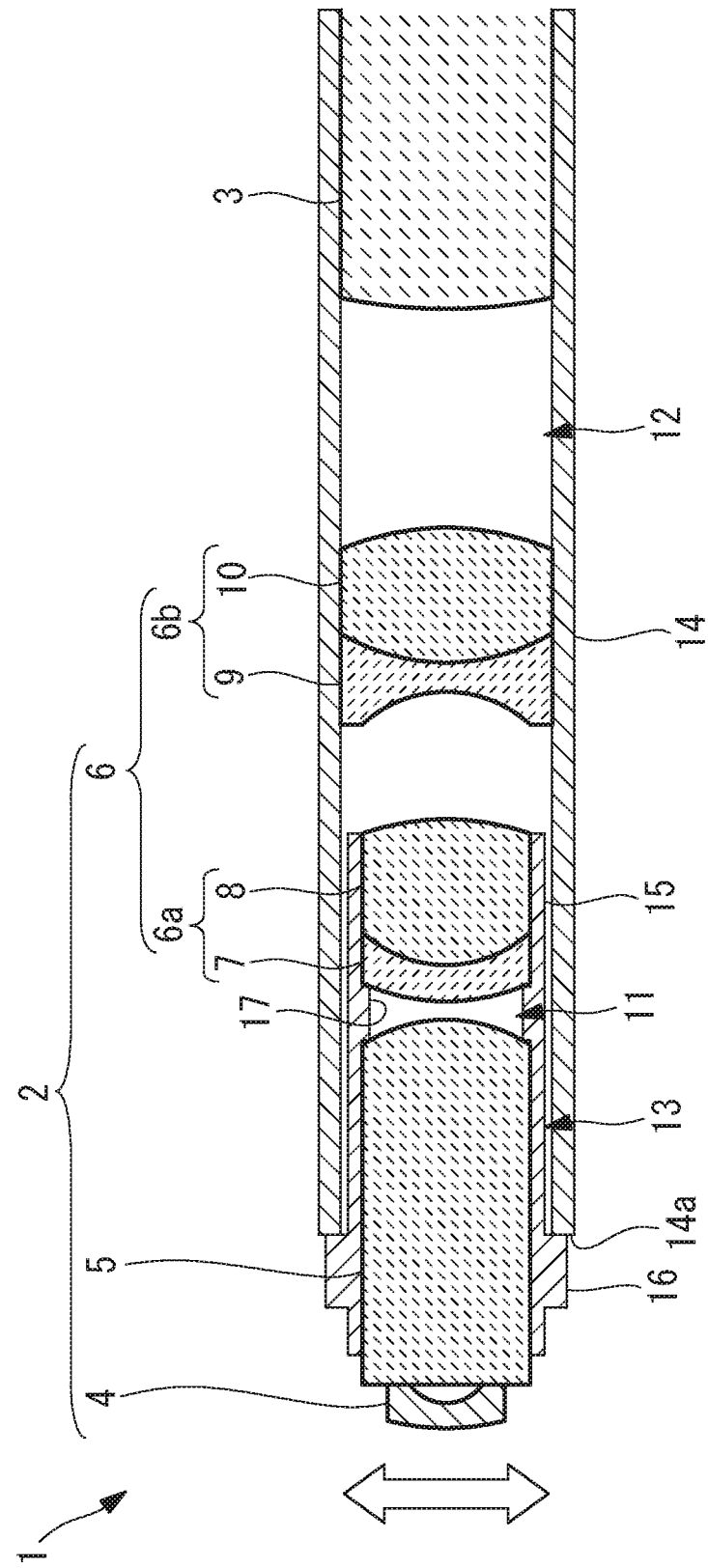
FIG. 1 is a partial vertical sectional view illustrating a rigid scope according to an embodiment of the present invention.

A rigid scope 1 according to an embodiment of the present invention will be described hereafter while referring to the drawings.

As illustrated in FIG. 1, the rigid scope 1 according to this embodiment includes an objective lens 2 and a relay lens 3 disposed in this order from the object side.

The objective lens 2 is composed of, in order from the object side, a first lens group 4 having a negative power, a second lens group 5 including a lens having a positive power, and a third lens group 6 including two or more lenses 7, 8, 9, and 10.

In the example illustrated in FIG. 1, the first lens group 4 consists of a meniscus lens that has a negative power and is composed of a single lens that is convex on the object side. The second lens group 5 consists of a single rod-shaped lens having a positive power. The third lens group 6 includes, in order from the object side, a doublet 6a consisting of a meniscus lens (lens) 7 and a biconvex lens (lens) 8 and a doublet (lens) 6b consisting of a biconcave lens (lens) 9 and a biconvex lens (lens) 10.

In this embodiment, the rigid scope 1 includes a first lens frame 13 that fixes in place a first group lens 11 including the first lens group 4, the second lens group 5, and the doublet 6a, which is on the object side of the third lens group 6, and includes a second lens frame 14 that fixes in place a second group lens 12 including the remaining lenses 9 and 10, i.e., the doublet 6b, which is on the image side of the third lens group 6, and the relay lens 3.

The second lens frame 14 is formed in a long cylindrical shape, and the second group lens 12 is fixed to an inner surface thereof.

The first lens frame 13 includes a cylindrical small-diameter part 15 having an outer diameter that is smaller than an inner diameter of the second lens frame 14 and a flange-shaped large-diameter part (protrusion) 16 that protrudes radially outward in the vicinity of a leading end of the small-diameter part 15.

Furthermore, a protrusion 17, which protrudes radially inward at a position partway along the longitudinal direction, is provided on an inner surface of the first lens frame 13. When the rod-shaped lens forming the second lens group 5 is inserted from the leading end side of the first lens frame 13, an end surface of the lens abuts against the protrusion 17 on the inner surface of the first lens frame 13 and is positioned in the optical axis direction. Furthermore, when the doublet 6a, which is on the object side of the third lens group 6, is inserted from the base end side of the first lens frame 13, an end surface of the doublet 6a abuts against the protrusion 17 and is positioned in the optical axis direction.

The outer diameter of the large-diameter part 16 is set so as to be larger than an inner diameter of the second lens frame 14. Abutting portions are formed by the large-diameter part 16 of the first lens frame 13 and a leading end surface 14a of the second lens frame 14.

Operation of the thus-configured rigid scope 1 according to this embodiment will be described below.

When manufacturing the rigid scope 1 according to this embodiment, a first unit is manufactured in advance by inserting the first group lens 11 along the inner surface of the first lens frame 13 and positioning and fixing the first group lens 11 with respect to the radial direction and the optical axis direction. In addition, a second unit is manufactured in advance by inserting the second group lens 12 along the inner surface of the second lens frame 14 and positioning and fixing the second group lens 12 with respect to the radial direction and the optical axis direction.

The first group lens 11 is positioned in the optical axis direction with respect to the second group lens 12 by inserting the small-diameter part 15 of the first unit manufactured using the first lens frame 13 from the leading end opening of the second lens frame 14 and abutting the large-diameter part 16 against the leading end surface 14a of the second lens frame 14. At this position, a gap is formed between the outer surface of the small-diameter portion 15 of the first lens frame 13 and the inner surface of the second lens frame 14 such that the first lens frame 13 and the second lens frame 14 can move in a direction perpendicular to the optical axis.

Next, image quality adjustment is performed in order to reduce image plane tilt by shifting the first unit with respect to the second unit in a direction perpendicular to the optical axis within the range of a radial direction gap formed between the first lens frame 13 and the second lens frame 14 due to the difference between the inner diameter of the second lens frame 14 and the outer diameter of the small-diameter part 15 of the first lens frame 13.

In this case, in the rigid scope 1 according to this embodiment, since the first lens group 4 having a large negative power and the second lens group 5 having a large positive power are fixed to the first lens frame 13 in advance, decentering of the first lens group 4 and the second lens group 5, which is a major cause of decentration comatic aberration, can be suppressed so as to be small. In addition, image plane tilt can be corrected by decentering the first group lens 11 with respect to the second group lens 12. Therefore, there is an advantage that image plane tilt can be corrected while suppressing the overall occurrence of decentration comatic aberration so as to be low.

The rigid scope 1 according to this embodiment is formed by fixing the first unit and the second unit to each other using an adhesive or the like in a state where the first unit and the second unit are positioned in the optical axis direction and image plane tilt is corrected.

In addition, in the rigid scope 1 according to this embodiment, since the first unit and the second unit are positioned in the optical axis direction by abutting the flange-shaped large-diameter part 16 of the first lens frame 13 and the leading end surface 14a of the second lens frame 14 against each other, there is an advantage in that the outer diameter of the second lens frame 14 can be minimized while securing a gap in the radial direction between the first lens frame 13 and the second lens frame 14, and the rigid scope 1 that has a small diameter can be formed. In addition, the process of forming the large-diameter part 16 on the outer surface of the first lens frame 13 can be simply performed.

Figure 2:
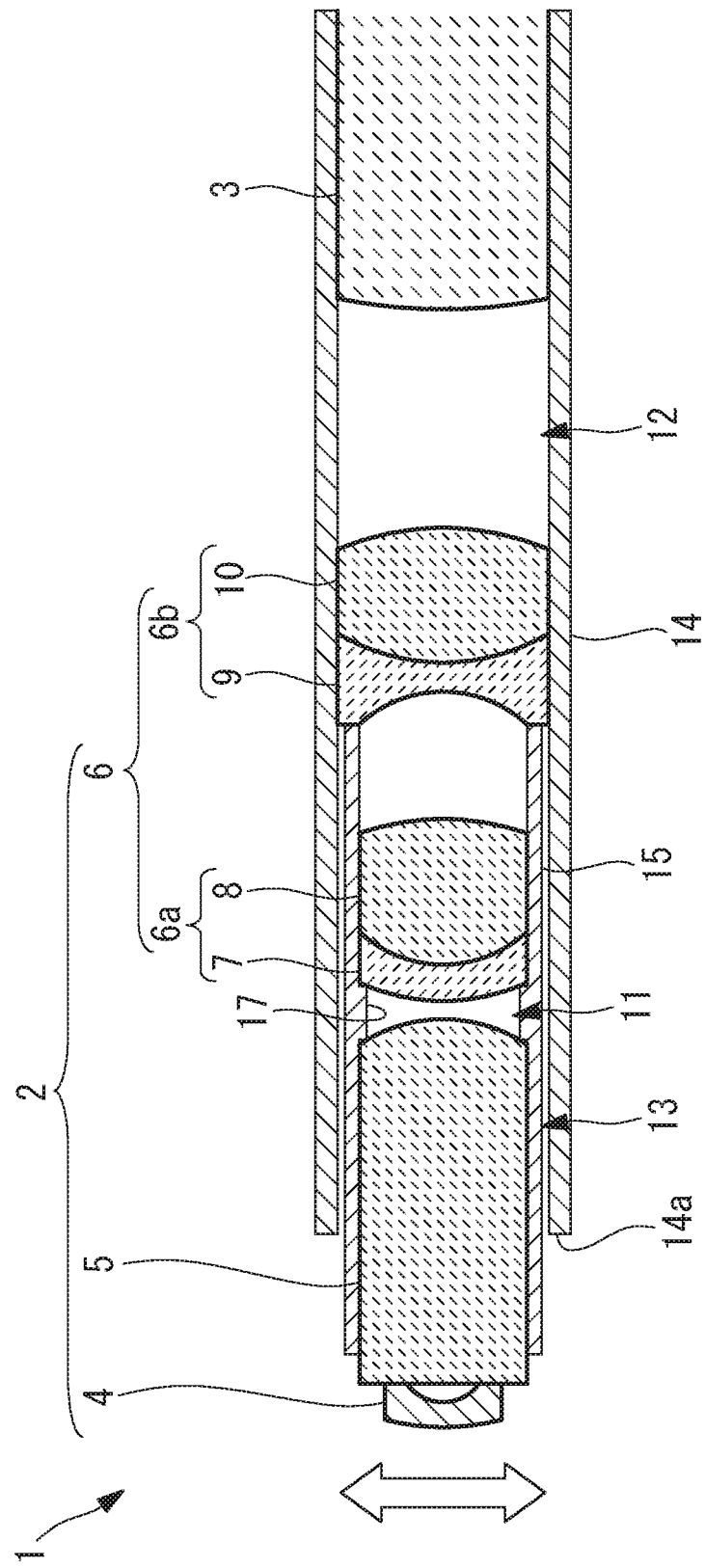
FIG. 2 is a partial vertical sectional view illustrating a first modification of the rigid scope in FIG. 1.

In addition, in this embodiment, although the abutting portions are formed by the large-diameter part 16 of the first lens frame 13 and the leading end surface 14a of the second lens frame 14, alternatively, as illustrated in FIG. 2, the base end of the first lens frame 13 may be made to extend toward the base end side and abut against a leading end surface of doublet 6b, which is on the image side of the third lens group 6, which is fixed inside the second lens frame 14. Thus, similarly, the first unit and the second unit can be easily positioned in the optical axis direction and the outer diameter of the second lens frame 14 can be minimized.

Figure 3:
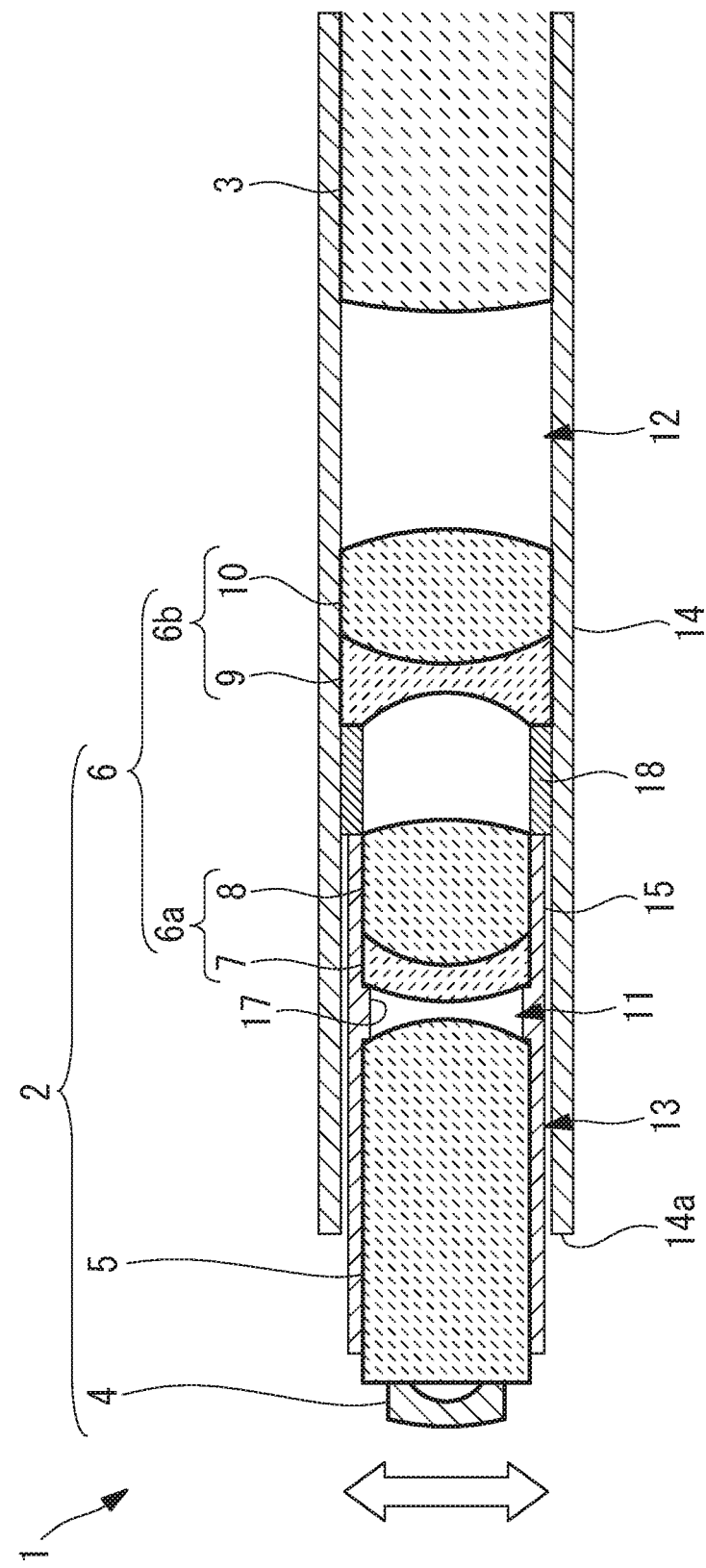
FIG. 3 is a partial vertical sectional view illustrating a second modification of the rigid scope in FIG. 1.

Furthermore, in FIG. 2, the part where the first lens frame 13 extends toward the base end side may instead be provided as a separate member, by as illustrated in FIG. 3, arranging a ring-shaped spacer (protrusion, abutting portion) 18 and a base end surface (abutting portion) of the first lens frame 13 may be made to abut against a leading end surface of the spacer 18 that abuts against the leading end surface of the doublet 6b, which is fixed inside the second lens frame 14. With this configuration as well, similarly, the first unit and the second unit can be positioned in the optical axis direction and the outer diameter of the second lens frame 14 can be minimized.

Figure 4:
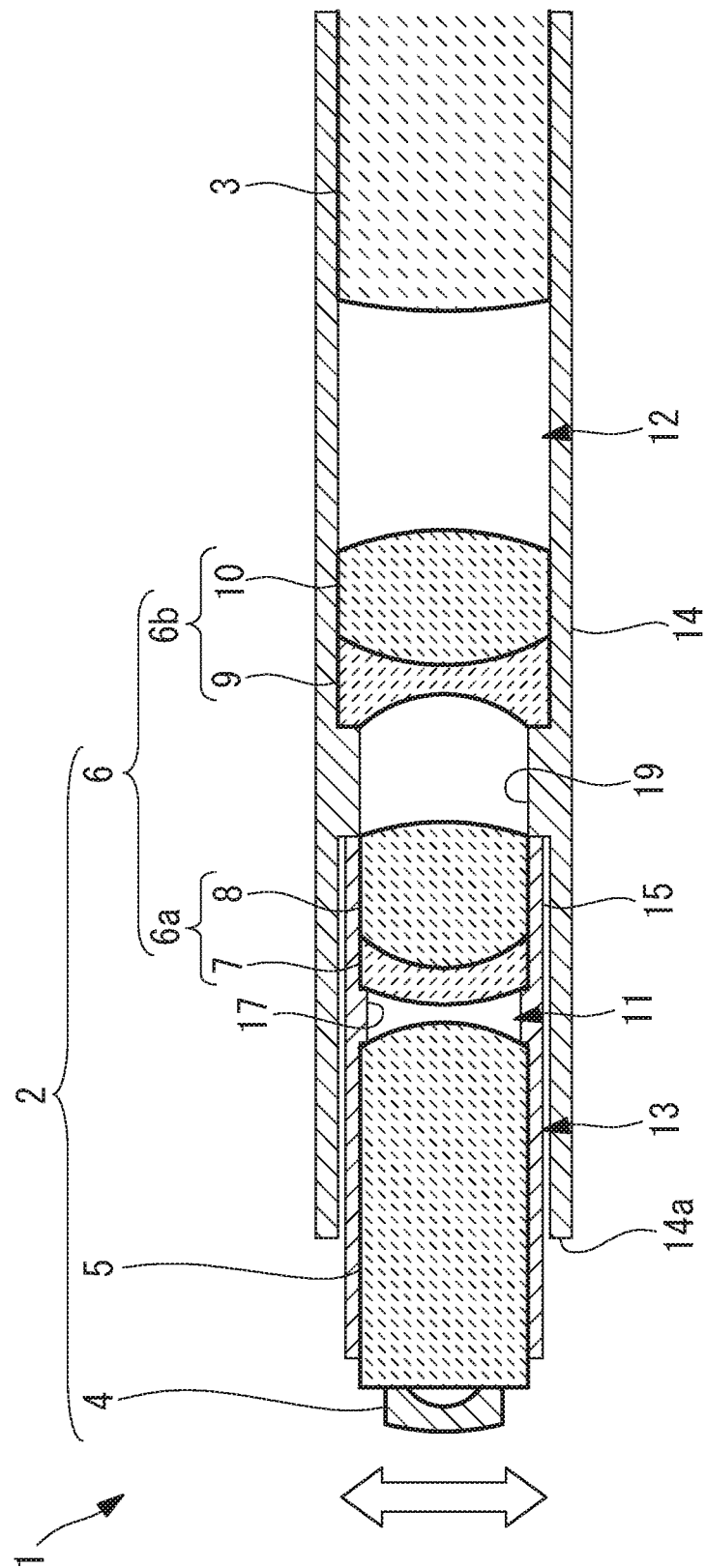
FIG. 4 is a partial vertical sectional view illustrating a third modification of the rigid scope in FIG. 1.

Furthermore, although the spacer 18 is formed of a separate member from the first lens frame 13 and the second lens frame 14, alternatively, a protrusion (abutting portion) 19 that protrudes radially inward may be formed on the inner surface of the second lens frame 14, as illustrated in FIG. 4. As a result of the base end surface (abutting portion) of the first lens frame 13 abutting against the leading end of the protrusion 19, similarly, the first unit and the second unit can be positioned in the optical axis direction and the outer diameter of the second lens frame 14 can be minimized.

Figure 5:
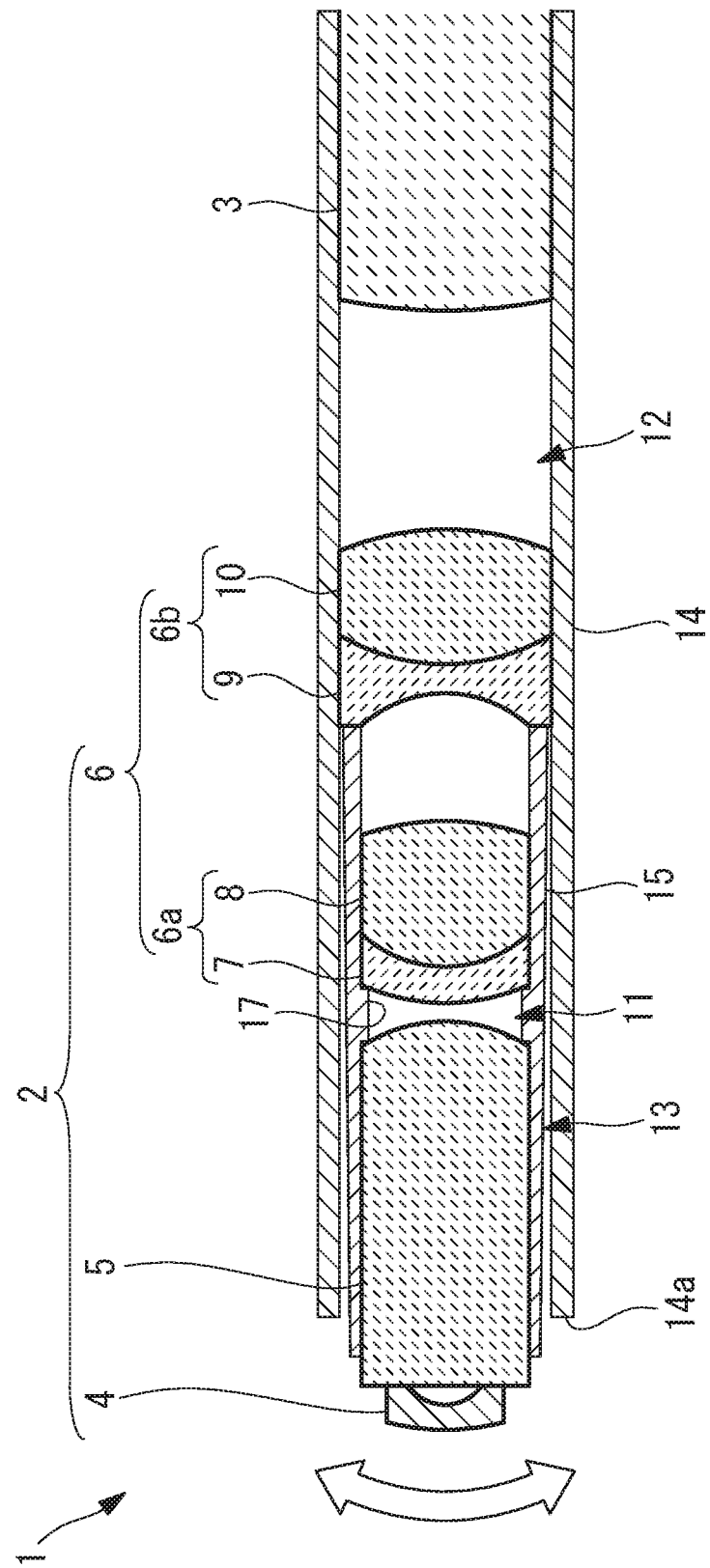
FIG. 5 is a partial vertical sectional view illustrating a fourth modification of the rigid scope in FIG. 1.

Furthermore, in this embodiment, image plane tilt is corrected by translationally moving the entire first lens frame 13 with respect to the second lens frame 14 within the range of the gap between the first lens frame 13 and the second lens frame 14, but alternatively, as illustrated in FIG. 5, the first lens frame 13 may have a tapered outer surface that tapers toward the leading end thereof.

With this configuration, the first unit, in particular, the region in the vicinity of the leading end thereof, can be moved by a large amount in a direction (direction indicated by arrows in figure) perpendicular to the optical axis by moving the leading end of the first lens frame 13 so as to be tilted around an axis that is perpendicular to the optical axis in a state where the base end surface of the first lens frame 13 is positioned in the optical axis direction and abuts against the leading end surface of the doublet 6b, which is fixed inside the second lens frame 14, similarly to as in FIG. 2. Therefore, similarly, image plane tilt can be corrected while suppressing the overall occurrence of decentration comatic aberration so as to be low.

Figure 6:
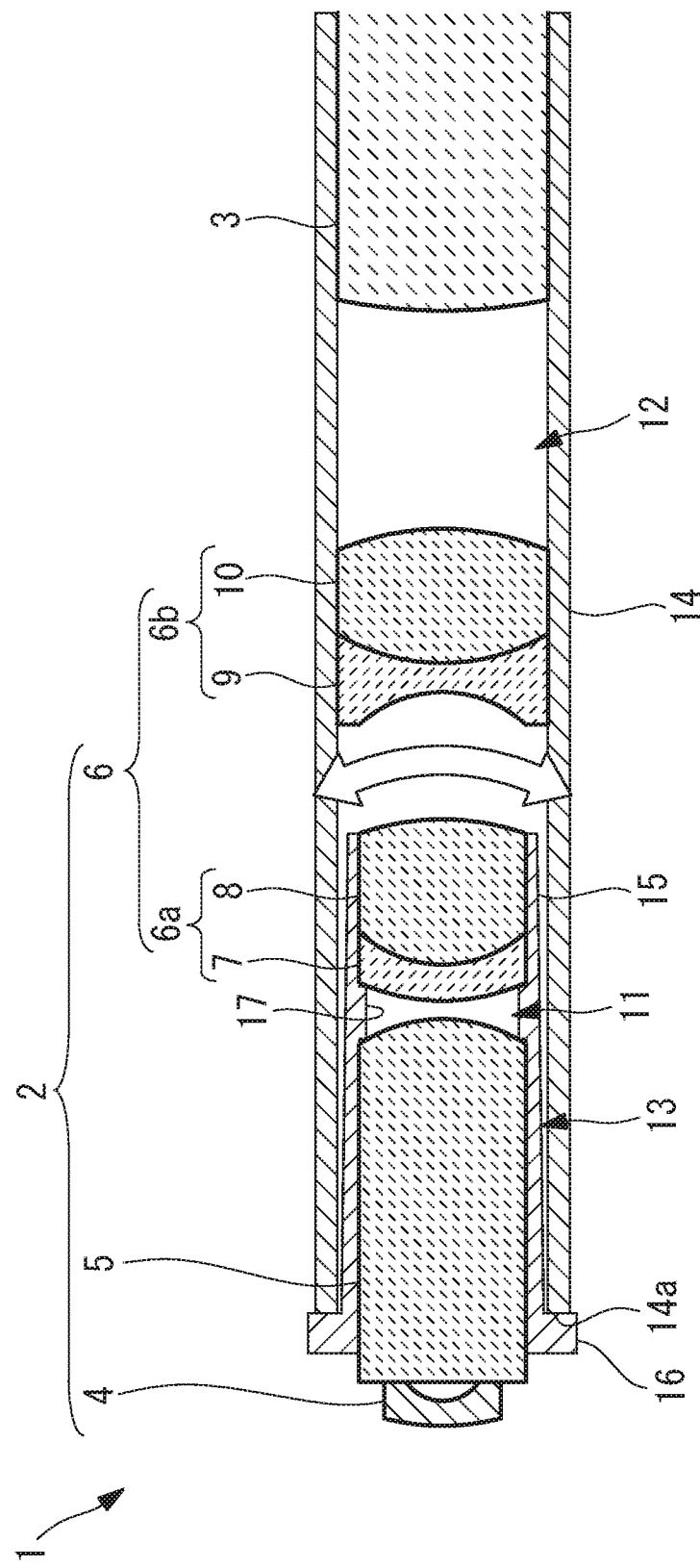
FIG. 6 is a partial vertical sectional view illustrating a fifth modification of the rigid scope in FIG. 1.

Furthermore, alternatively, as illustrated in FIG. 6, the first lens frame 13 may have a tapered outer surface that tapers toward the base end thereof. In this case, the first unit, in particular, the region in the vicinity of the base end thereof, can be moved by a large amount in a direction (direction indicated by arrows in figure) perpendicular to the optical axis by moving the base end of the first lens frame 13 so as to be tilted around an axis that is perpendicular to the optical axis in a state where the flange-shaped large-diameter part 16 provided at the leading end abuts against the leading end surface 14a of the second lens frame 14 and the first unit and the second unit are positioned in the optical axis direction. Therefore, similarly, image plane tilt can be corrected while suppressing the overall occurrence of decentration comatic aberration so as to be low.

Figure 7:
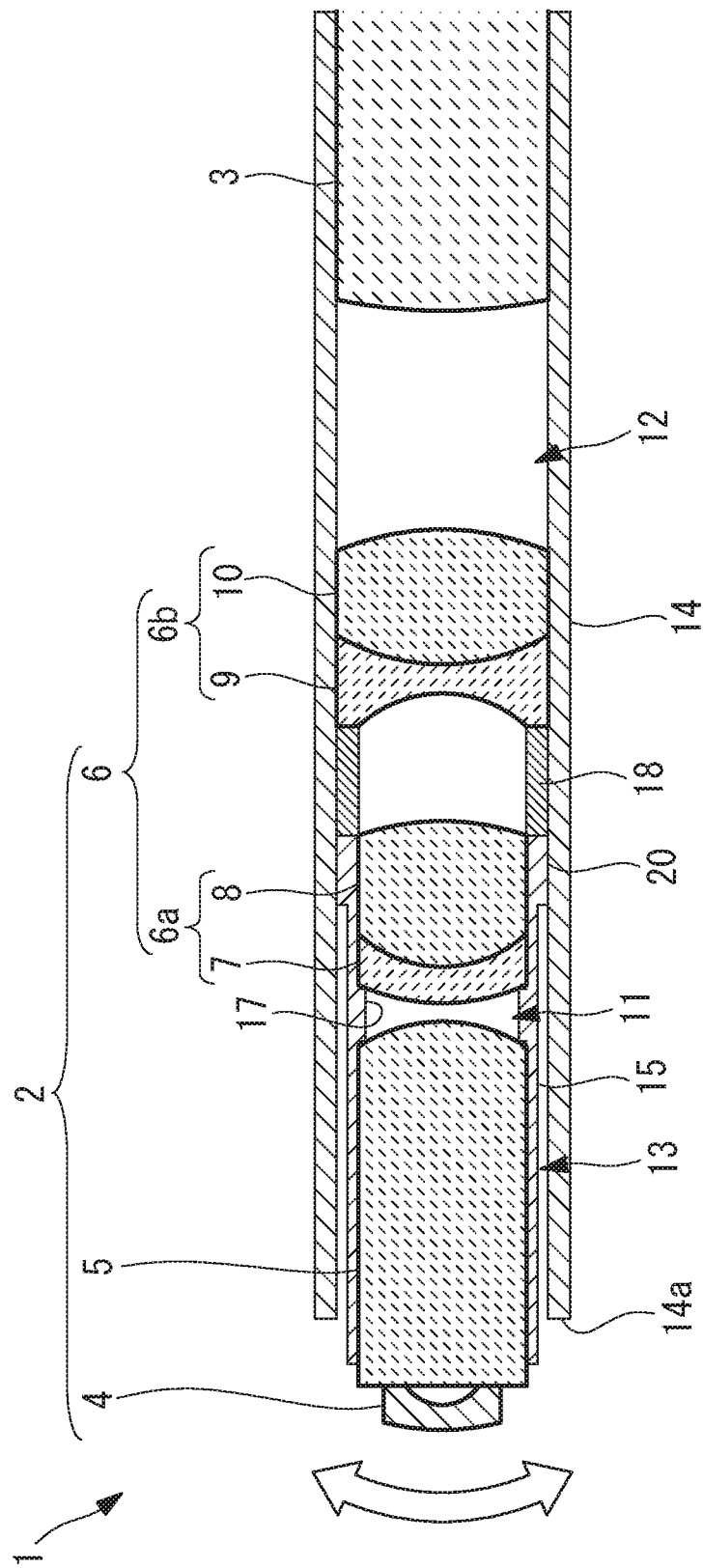
FIG. 7 is a partial vertical sectional view illustrating a sixth modification of the rigid scope in FIG. 1.
Figure 8:
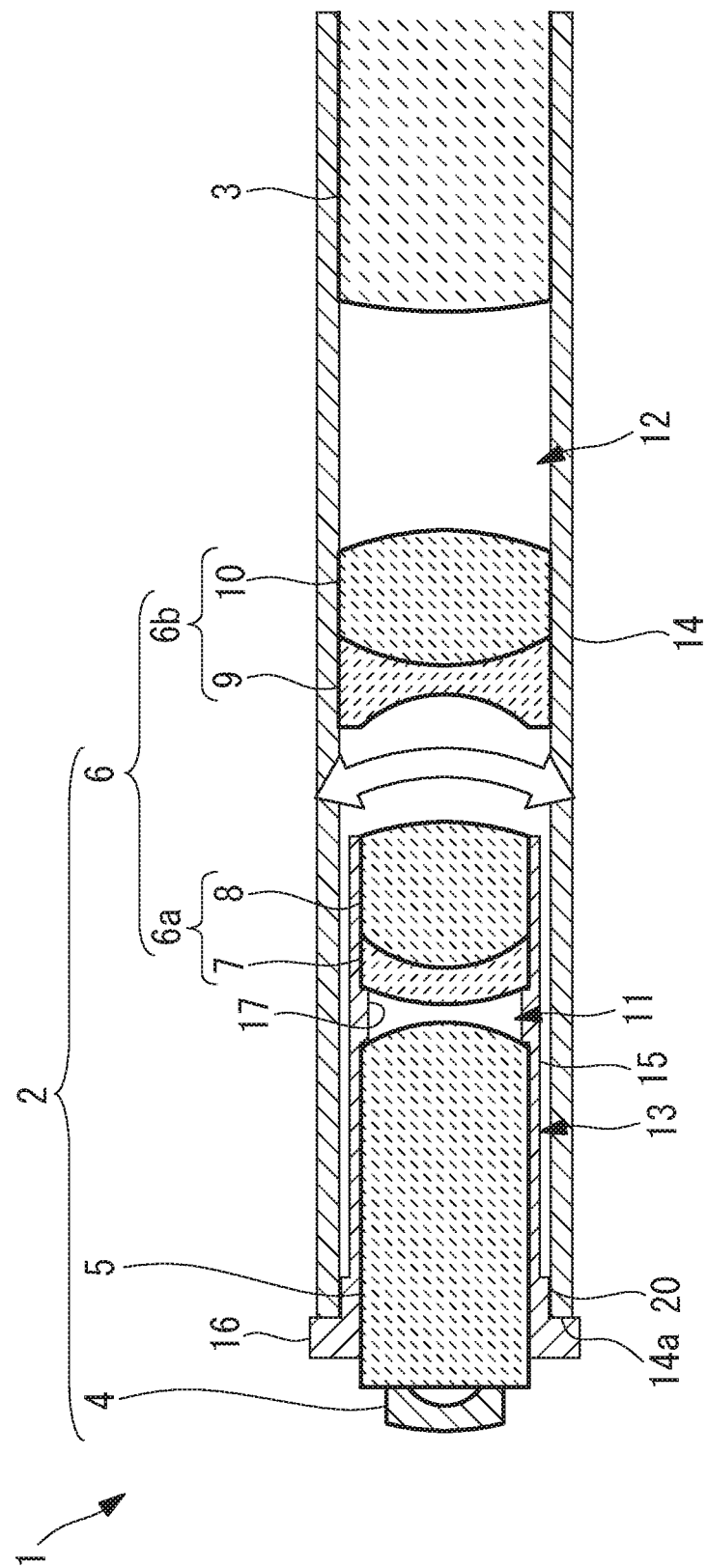
FIG. 8 is a partial vertical sectional view illustrating a seventh modification of the rigid scope in FIG. 1.

Furthermore, instead of the first lens frame 13 having a tapered outer surface, as illustrated in FIGS. 7 and 8, a projecting portion (abutting portion) 20 having a diameter that is larger than that of the small-diameter part 15 and allows the projecting portion 20 to be inserted into the inside of the second lens frame 14 may be provided at either end of the small-diameter part 15 in the longitudinal direction. With this configuration as well, the first lens frame 13 can be tilted with respect to the second lens frame 14 with the projecting portion 20 acting as a fulcrum so as to be tilted around an axis perpendicular to the optical axis, and the same effect as described above can be obtained.

Figure 9:
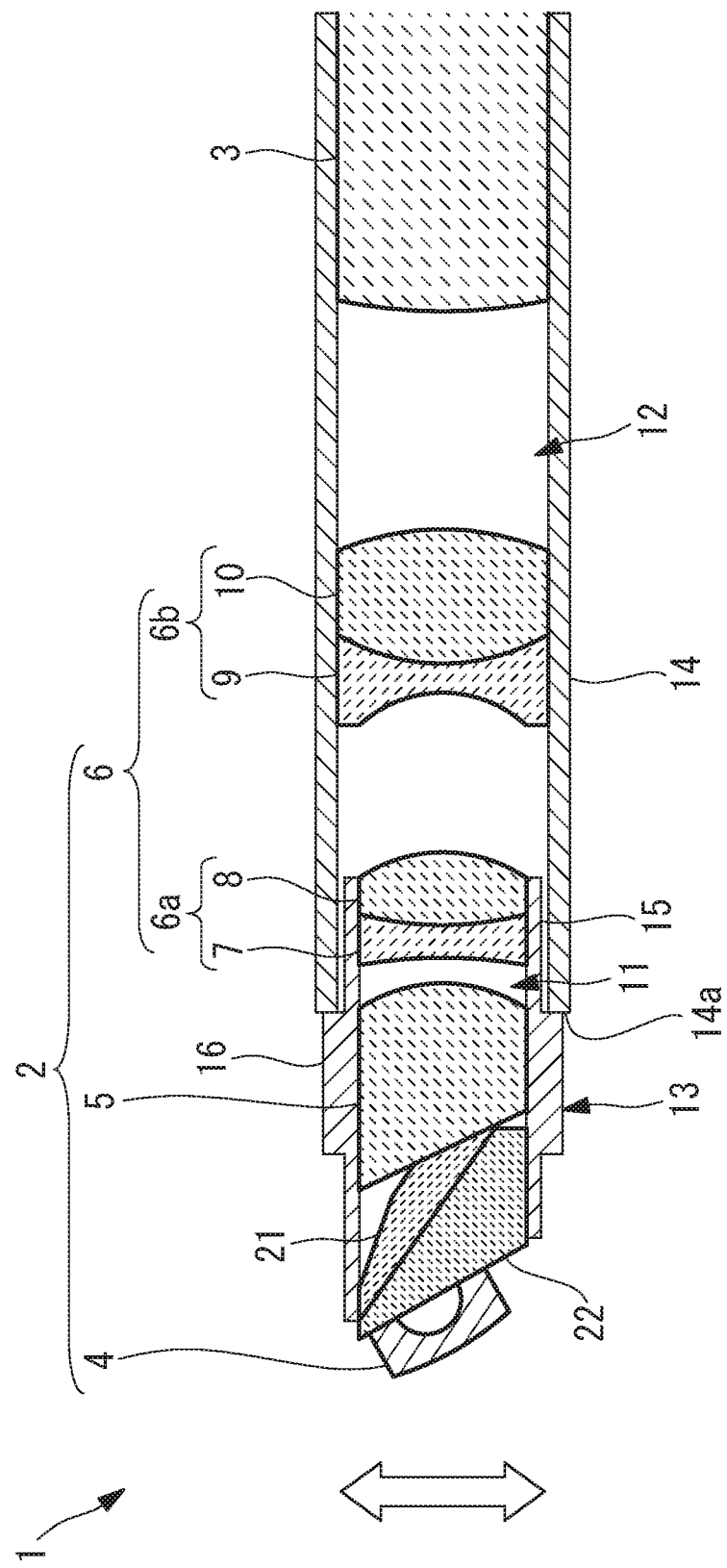
FIG. 9 is a partial vertical sectional view illustrating an eighth modification of the rigid scope in FIG. 1.
Figure 10:
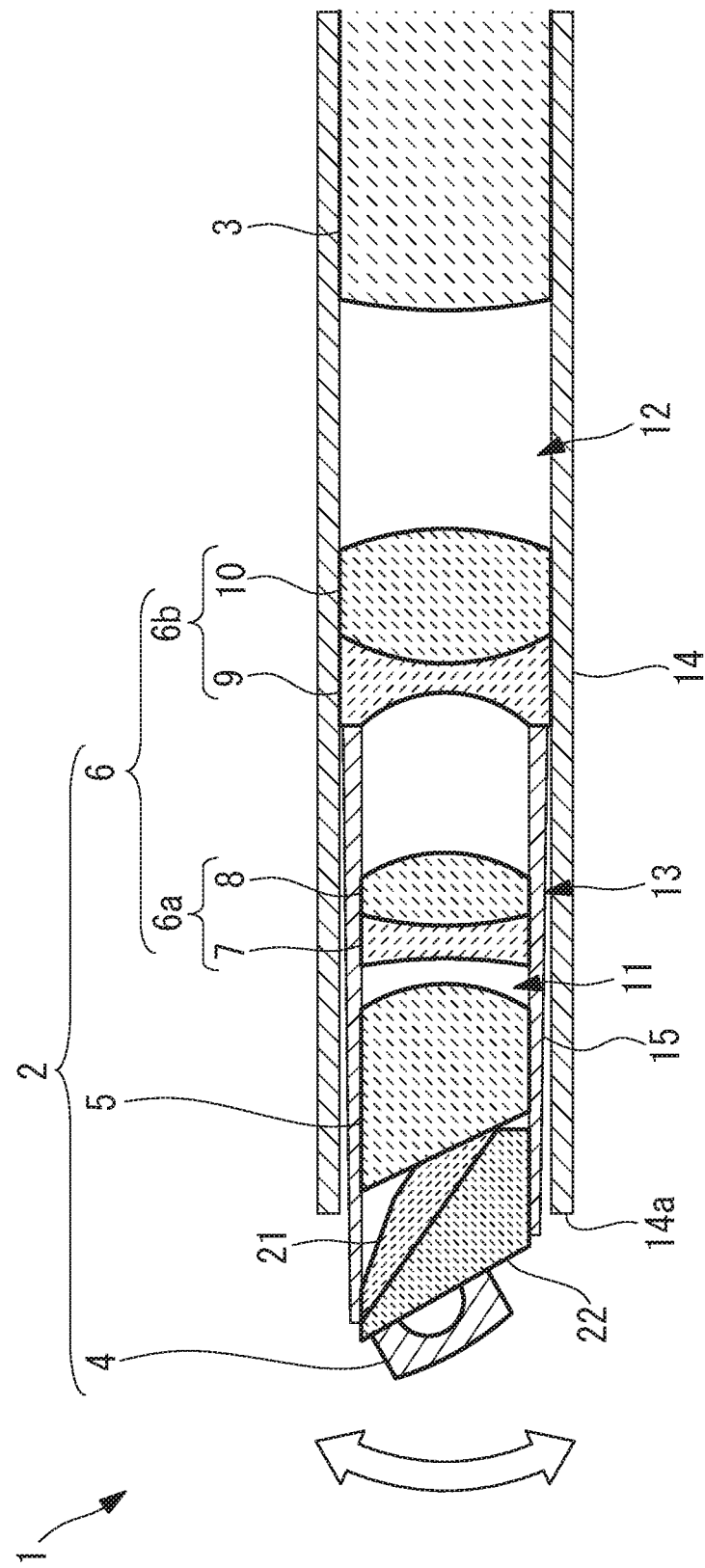
FIG. 10 is a partial vertical sectional view illustrating a ninth modification of the rigid scope in FIG. 1.

In addition, a rod-shaped positive power single lens has been exemplified as the second lens group 5 in this embodiment, but alternatively, the second lens group 5 may include a positive power lens 21 that is bonded to a field-of-view-direction changing prism 22 as illustrated in FIGS. 9 and 10. With this configuration, there is an advantage in that image plane tilt can be corrected while suppressing the overall occurrence of decentration comatic aberration so as to be low in an oblique-viewing-type rigid scope 1.

In addition, in this embodiment, the first lens group 4 and the second lens group 5 are each formed of a single lens, but alternatively, the first lens group 4 and the second lens group 5 may each include a plurality of lenses.

Furthermore, the first group lens 11 consisting of the first lens group 4, the second lens group 5, and the doublet 6a of the third lens group 6 is fixed to the first lens frame 13, but alternatively only the first lens group 4 and the second lens group 5 may be fixed to the first lens frame 13 as the first group lens 11.

In addition, the third lens group 6 is formed of two doublets 6a and 6b and one doublet 6a is fixed to the first lens frame 13, but alternatively the third lens group 6 may be formed of three or more single lenses or doublets and part of the third lens group 6 consisting of two or more singles lenses or doublets may be fixed to the first lens frame 13.

Figure 11:
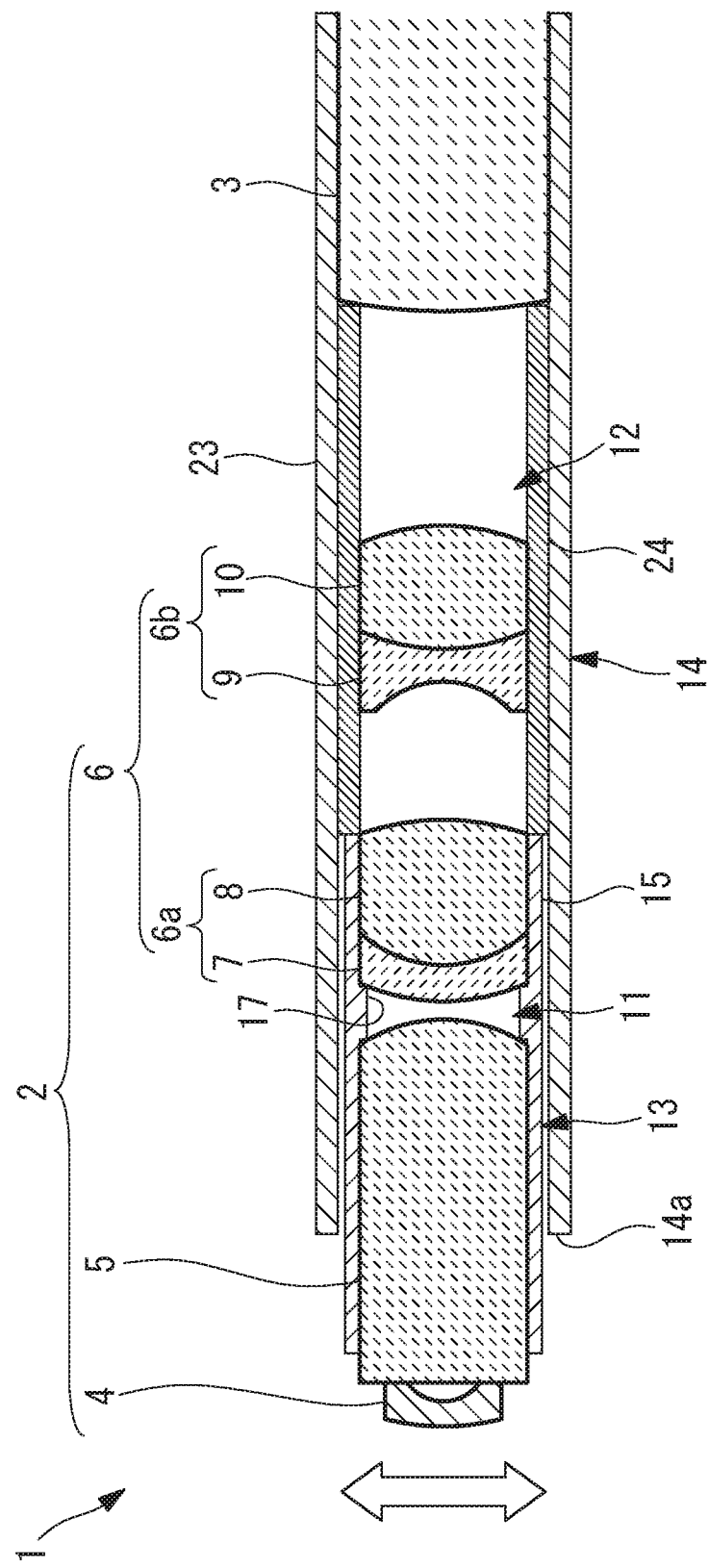
FIG. 11 is a partial vertical sectional view illustrating a tenth modification of the rigid scope in FIG. 1.

Furthermore, a lens frame consisting of a single cylindrical member is exemplified as the second lens frame 14 in this embodiment, but alternatively as illustrated in FIG. 11, a lens frame consisting of an outer cylinder 23 having an inner diameter that is larger than the outer diameter of the first lens frame 13 and an inner cylinder (abutting portion) 24 having an outer diameter that is slightly smaller than the inner diameter of the inside of the outer cylinder 23 and an inner diameter that is smaller than the outer diameter of the first lens frame 13 may be employed as the second lens frame 14.

In this case, the relay lens 3 is fixed to the outer cylinder 23 of the second lens frame 14 and the doublet 6b is fixed to the inner cylinder 24 of the second lens frame 14. When the inner cylinder 24 is inserted into the outer cylinder 23 from the leading end side, the base end of the inner cylinder 24 abuts against the relay lens 3, thus forming the second lens frame 14. In this state, when the first lens frame 13 is inserted into the outer cylinder 23 of the second lens frame 14, the base end of the first lens frame 13 abuts against the leading end of the inner cylinder 24 of the second lens frame 14.

As a result, the above-described embodiment also leads to the following aspect.

An aspect of the present invention is directed to a rigid scope that includes: an objective lens including, in order from an object side to an image side, a first lens group having a negative power, a second lens group including a lens having a positive power, and a third lens group including two or more lenses; a relay lens arranged on the image side of the objective lens; a first lens frame that fixes in place a first group lens including at least the first lens group and the second lens group of the objective lens; and a second lens frame that fixes in place a second group lens including one or more remaining lenses of the objective lens and at least part of the relay lens. A gap is provided between the first lens frame and the second lens frame so as to allow relative movement therebetween in a direction perpendicular to an optical axis in a state where the first lens frame is positioned in an optical axis direction so as to abut against the second lens frame.

According to this aspect, light from the subject is collected from a wide field of view by the first lens group having a negative power, is collected by the second lens group having a positive power, and passes through the third lens group, and the light is then relayed by the relay lens and captured by an imaging element. When forming the rigid scope, the first group lens including the first lens group and the second lens group is fixed in place by the first lens frame and the remaining second group lens is fixed in place by the second lens frame.

The first group lens and the second group lens can be positioned in the optical axis direction by abutting the first lens frame, which supports the first group lens, in the optical axis direction against the second lens frame, which supports the second group lens. In addition, in this state, image quality adjustment can be performed in order to reduce image plane tilt by moving the first lens frame relative to the second lens frame in a direction perpendicular to the optical axis within the range of the gap between the first lens frame and the second lens frame.

In this case, decentering of the first lens group and the second lens group, which is a major cause of decentration comatic aberration, can be suppressed so as to be small in advance by fixing the first lens group having a large negative power and the second lens group having a large positive power to the first lens frame in advance. Therefore, the overall occurrence of decentration comatic aberration can be suppressed to be low even when image plane tilt is corrected by decentering the first group lens relative to the second group lens.

In this aspect, the second lens group may include a rod-shaped lens having a positive power.

With this configuration, image plane tilt correction can be performed while suppressing the overall occurrence of decentration comatic aberration so as to be low in a direct-viewing-type rigid scope.

In the above-described aspect, the second lens group may include a positive power lens that is bonded to a field-of-view-direction changing prism.

With this configuration, image plane tilt correction can be performed while suppressing the overall occurrence of decentration comatic aberration so as to be low in an oblique-viewing-type or lateral-viewing-type rigid scope.

In the above-described aspect, the first lens frame and the second lens frame may be formed in cylindrical shapes, the second lens frame may have an inner diameter that is larger than an outer diameter of the first lens frame, and the first lens frame and the second lens frame may be provided with abutting portions that position the first lens frame and the second lens frame by abutting against each other in the optical axis direction.

With this configuration, the abutting portions provided on the first lens frame and the second lens frame abut against each other and position the first lens frame and the second lens frame in the optical axis direction and image plane tilt correction can be performed while suppressing overall occurrence of decentration comatic aberration by moving the first lens frame relative to the second lens frame in a direction perpendicular to the optical axis within a range of a difference between the outer diameter of the first lens frame and the inner diameter of the second lens frame.

In the above-described aspect, the abutting portions may consist of a protrusion that projects radially outward in the vicinity of a leading end of the first lens frame and a leading end surface of the second lens frame that abuts against the protrusion in the optical axis direction.

With this configuration, the first group lens and the second group lens can be easily positioned in the optical axis direction by making the protrusion of the first lens frame and the leading end surface of the second lens frame abut against each other and the outer diameter of the second lens frame can be minimized.

In the above-described aspect, the abutting portions may consist of a protrusion that protrudes radially inward from an inner surface of the second lens frame and a base end surface of the first lens frame that abuts against the protrusion in the optical axis direction.

With this configuration, the first group lens and the second group lens can be easily positioned in the optical axis direction by abutting the protrusion of the second lens frame and the base end surface of the first lens frame against each other.

In the above-described aspect, the protrusion may be a spacer that is inserted at a position so as to abut against a leading end of the second group lens inside the second lens frame.

With this configuration, the first group lens and the second group lens can be easily positioned in the optical axis direction by abutting the base end surface of the first lens frame against the spacer inserted at a position so as to abut against the leading end of the second group lens inside the second lens frame.

In the above-described aspect, at least one end in the optical axis direction may be capable of being moved in a direction perpendicular to the optical axis by tilting the first lens frame relative to the second lens frame around an axis that is perpendicular to the optical axis.

With this configuration, one end of the first lens frame in the optical axis direction can be moved in a direction perpendicular to the optical axis by tilting the first lens frame relative to the second lens frame within the range of the gap.

The present invention affords the advantage that image quality can be adjusted so as to reduce image plane tilt while suppressing performance degradation of center image quality so as to be low.

REFERENCE SIGNS LIST 1 rigid scope
2 objective lens
3 relay lens
4 first lens group
5 second lens group
6 third lens group
7 meniscus lens (lens)
8 biconvex lens (lens)
9 biconcave lens (lens)
10 biconvex lens (lens)
11 first group lens
12 second group lens
13 first lens frame
14 second lens frame
14a leading end surface (abutting portion)
16 large-diameter part (protrusion, abutting portion)
18 spacer (protrusion, abutting portion)
19 protrusion (abutting portion)
20 projecting portion (abutting portion)
21 lens
22 field-of-view-direction changing prism
24 inner cylinder (abutting portion)

The invention claimed is:

1. A rigid scope comprising:
an objective lens composed of, in order from an object side to an image side, a first lens group having a negative refractive power, a second lens group including a lens having a positive refractive power, and a third lens group including at least two lenses;
a relay lens arranged on the image side of the objective lens;
a first lens frame that fixes in place a front group including at least the first lens group and the second lens group of the objective lens; and
a second lens frame that fixes in place a rear group including (i) at least one remaining lens of the objective lens other than the first lens group and the second lens group and (ii) at least part of the relay lens,
wherein the first lens frame and the second lens frame are fixed to each other in a state in which image plane tilt is corrected by the first lens frame abutting against the second lens frame in an optical axis direction and by relatively moving the first lens frame and the second lens frame within a gap between the first lens frame and the second lens frame in a direction perpendicular to the optical axis.

2. The rigid scope according to claim 1, wherein the second lens group includes a rod-shaped lens having a positive refractive power.

3. The rigid scope according to claim 1, wherein the second lens group includes a positive refractive power lens that is bonded to a field-of-view-direction changing prism.

4. The rigid scope according to claim 1, wherein:
the first lens frame and the second lens frame have cylindrical shapes,
an inner diameter of the second lens frame is larger than an outer diameter of the first lens frame, and
at least one of the first lens frame and the second lens frame is provided with an abutting portion that positions the first lens frame and the second lens frame by the first lens frame and the second lens frame abutting against each other in the optical axis direction.

5. The rigid scope according to claim 4, wherein the abutting portion comprises a protrusion that projects radially outward in a vicinity of a leading end of the first lens frame and a leading end surface of the second lens frame that abuts against the protrusion in the optical axis direction.

6. The rigid scope according to claim 4, wherein the abutting portion comprises a protrusion that protrudes radially inward from an inner surface of the second lens frame and a base end surface of the first lens frame that abuts against the protrusion in the optical axis direction.

7. The rigid scope according to claim 6, wherein the protrusion comprises a spacer that is inserted at a position so as to abut against a leading end of the rear group inside the second lens frame.

8. The rigid scope according to claim 1, wherein at least one end in the optical axis direction is configured to be moved in a direction perpendicular to the optical axis by tilting the first lens frame relative to the second lens frame around an axis that is perpendicular to the optical axis.

* * * * *